United States Patent [19]
Acker et al.

[11] 4,410,465
[45] Oct. 18, 1983

[54] PREPARATION OF BUTADIENE DINITRILES

[75] Inventors: Rolf-Dieter Acker, Leimen; Gerhard Hamprecht, Weinheim, both of Fed. Rep. of Germany

[73] Assignee: BASF Aktiengesellschaft, Fed. Rep. of Germany

[21] Appl. No.: 338,113

[22] Filed: Jan. 8, 1982

[30] Foreign Application Priority Data

Jan. 30, 1981 [DE] Fed. Rep. of Germany ....... 3103066

[51] Int. Cl.$^3$ .................. C07C 120/00; C07C 121/30
[52] U.S. Cl. ............................................. 260/465.5 R
[58] Field of Search ................................ 260/465.5 R

[56] References Cited

U.S. PATENT DOCUMENTS 3,974,159  8/1976  Decker et al. ...................... 544/177

FOREIGN PATENT DOCUMENTS 2430353  1/1976  Fed. Rep. of Germany .

OTHER PUBLICATIONS

Synthesis (1979), pp. 326–378; Ege et al.

Primary Examiner—Joseph Paul Brust
Attorney, Agent, or Firm—Keil & Witherspoon

[57] ABSTRACT

Butadiene dinitriles are prepared by reacting a quaternary ammonium compound with malodinitrile in the presence of an alkanol and then reacting the product with an alkali metal compound.

The butadiene dinitriles obtainable by the process of the invention are valuable starting materials for the preparation of dyes, pesticides, drugs and vitamins.

8 Claims, No Drawings

PREPARATION OF BUTADIENE DINITRILES

The present invention relates to a process for the preparation of butadiene dinitriles by reacting a quaternary ammonium compound with malodinitrile in the presence of an alkanol and then reacting the product with an alkali metal compound.

The preparation of quaternary ammonium compounds, which are also derivatives of malonaldehyde, of the formula

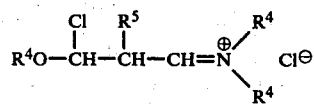

where $R^4$ is alkyl and $R^5$ is alkyl or H, by reacting phosgene with a dialkylformamide to give dialkylformamidechloride and then reacting this product with an enol ether has been disclosed (German Laid-Open Application DOS No. 2,424,373).

Furthermore, it is known (Synthesis 1979, pages 376 to 378) that alkylidenemalodinitriles can be reacted with lithium-diisopropylamide in tetrahydrofuran at $-65°$ C. and the product then reacted with dimethylformamide-dichloride to give 4-dimethylamino-1,3-butadiene-1,1-dicarbonitrile. These butadiene compounds can be converted to 2-aminopyridines by reaction with ammonia in methanol.

We have found that butadiene dinitriles of the formula

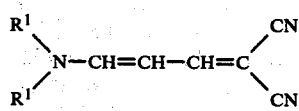

where the radicals $R^1$ are identical or different and each is an aliphatic radical, are advantageously obtained if a quaternary ammonium compound of the formula

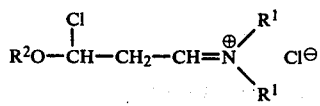 II where $R^1$ has the above meaning and $R^2$ is an aliphatic radical, (a) is reacted with malodinitrile in the presence of alkanols and (b) the reaction mixture is then reacted with an alkali metal compound, If N,N-(3-chloro-3-ethoxypropylidene)-N,N-dimethyl-ammonium chloride is used, the reaction can be represented by the following equation:

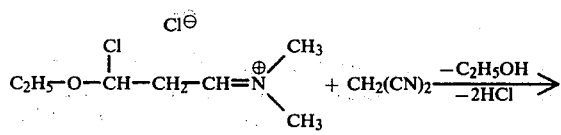

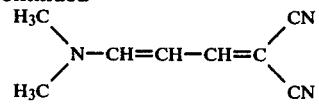

Compared to the known processes, the process according to the invention gives butadiene dinitriles by a simpler and more economical route, in good yield and purity and with better overall space-time yield. Reactants which are difficult to obtain are avoided, such as lithium compounds. All these advantageous results are surprising in view of the prior art.

The starting material II is readily prepared by the process described in German Laid-Open Application DOS No. 2,424,373, referred to above. It can be reacted with the malodinitrile in stoichiometric amount or in excess, advantageously in a ratio of from 0.5 to 3, preferably from 0.8 to 1.5, moles of malodinitrile per mole of starting material II. Preferred starting materials II and, accordingly, preferred end products I are those in whose formulae $R^1$ and $R^2$ are identical or different and each is alkyl of 1 to 7 carbon atoms, preferably of 1 to 4 carbon atoms, in particular methyl and ethyl. The above radicals can also be substituted by groups which are inert under the reaction conditions, eg. alkyl or alkoxy of 1 to 4 carbon atoms each, thus when alkyl of 1 to 4 carbons is substituted on alkyl of 1 to 7 carbon atoms the total alkyl group substituent may contain up to eleven carbon atoms.

Examples of suitable starting materials II are thus N,N-(3-chloro-3-ethoxy-propylidene)-N,N-dimethylammonium chloride; the N,N-diethyl, N,N-dipropyl, N,N-diisopropyl, N,N-dibutyl, N,N-diisobutyl, N,N-di-sec.-butyl and N,N-di-tert.-butyl derivatives; and corresponding 3-methoxy, 3-propoxy, 3-isopropoxy, 3-butoxy, 3-sec.-butoxy and 3-tert.-butoxy derivatives.

The alkanols used in stage (a) advantageously contain 1 to 10, in particular 1 to 6, carbon atoms, and examples of suitable alkanols are methyl, ethyl, propyl, isopropyl, butyl, isobutyl, sec.-butyl, tert.-butyl alcohol, the first-mentioned being preferred. From 1 to 1,000, particularly from 10 to 100, moles of alkanol are advantageously used per mole of starting material II, and malodinitrile is advantageously employed in a ratio of from 0.5 to 3.0, preferably from 0.5 to 1.5, moles per mole of starting material II.

In stage (b), the reaction mixture is reacted with an alkali metal compound, preferably an alkali metal hydroxides, alkali metal carbonate and/or alkali metal alcoholate, in particular sodium carbonate, potassium carbonate, sodium hydroxide solution and potassium hydroxide solution. It is advantageous to use saturated aqueous alkali metal carbonate solutions or from 0.1 to 10 molar aqueous NaOH or KOH, with or without the addition of more water. Altogether, a ratio of from 5 to 500, in particular from 10 to 100, moles of water and/or from 0.2 to 10, in particular from 0.5 to 2, equivalents of alkali metal compound per mole of starting material II is advantageous. Examples of suitable alkali metal compounds are potassium hydroxide, sodium hydroxide, potassium carbonate, sodium carbonate, lithium hydroxide, lithium carbonate, sodium bicarbonate, potassium bicarbonate, sodium formate, sodium acetate, sodium propionate, sodium butyrate, sodium isobutyrate, potassium formate, potassium acetate, potassium propionate, potassium butyrate, potassium isobutyrate, sodium methylate, sodium ethylate, sodium propylate, sodium isopropylate, sodium butylate, sodium isobutylate, sodium sec.-butylate, sodium tert.-butylate, sodium ethylene glycolate, sodium propylene-1,2-glycolate, sodium propylene-1,3-glycolate, sodium diethylene glycolate, sodium triethylene glycolate, sodium dipropylene-1,2-glycolate, potassium methylate, potassium ethylate, potassium n-propylate, potassium isopropylate, potassium n-butylate, potassium isobutylate, potassium sec.-butylate, potassium tert.-butylate, potassium ethylene glycolate, potassium propylene-1,2-glycolate, potassium diethylene glycolate, potassium triethylene glycolate and potassium dipropylene-1,2-glycolate.

As a rule, the reaction in stage (a) is carried out at from 40° to 140° C., preferably from 60° to 120° C., depending on the alkanol used, and in stage (b) at from −10° to +50° C., preferably from −5° to +30° C., under atmospheric pressure or under superatmospheric pressure, continuously or batchwise.

The reaction can be carried out as follows: a mixture of starting material II, malodinitrile and alkanol is kept at the reaction temperature of stage (a) for from 2 to 10 hours. Sodium carbonate solution and water are then added, and the mixture is kept at the reaction temperature of stage (b) for from 0.1 to 3 hours. The end product can be separated off in a conventional manner, for example by extraction.

The butadiene dinitriles obtainable by the process of the invention are valuable starting materials for the preparation of dyes, pesticides, drugs and vitamins. Thus, they can be converted by reaction with ammonia in the presence of alkanols to aminonicotinonitriles, and these compounds can be converted into the aminonicotinic acids by reaction with alkali. The latter compounds are used as starting materials for the pesticides described in German Laid-Open Application DOS No. 2,430,353 (laid open Jan. 15, 1976).

In the Examples which follow parts are by weight.

EXAMPLE 1

(a) 20 parts of N,N-(3-chloro-3-ethoxy-propylidene)-N,N-dimethylammonium chloride, 6.6 parts of malodinitrile and 80 parts of methanol are refluxed for 5 hours.

(b) After the solvent has been distilled off, 20 parts of water are added and the mixture is adjusted to pH 7 with saturated $Na_2CO_3$ solution. Extraction with methylene chloride gives 13.1 parts of an oil, from which 12.0 parts (81% of theory) of 1,1-dicyano-4-N,N-dimethylamino-1,3-butadiene, of melting point 129°–132° C., are obtained after filtration.

EXAMPLE 2

(a) 220 parts of N,N-(3-chloro-3-isobutoxy-propylidene)-N,N-dimethylammonium chloride, 66 parts of malodinitrile and 800 parts of methanol are refluxed at approximately 66° C. for 6 hours.

(b) After the solvent has been distilled off, 200 parts of water are added and the mixture is adjusted to pH 7 with saturated $Na_2CO_3$ solution. Extraction with methylene chloride gives an oily residue which crystallizes on adding methanol and cooling. 111 parts (75% of theory) of 1,1-dicyano-4-N,N-dimethylamino-1,3-butadiene are obtained after filtration.

EXAMPLE 3

The reaction is carried out analogously to Example 1. After stage (a), the solvent is distilled off, 30 parts of water are added and the mixture is adjusted to pH 7 with 2 molar sodium hydroxide solution. Extraction with methylene chloride and crystallization with methanol give 11.5 parts (77% of theory) of 1,1-dicyano-4-N,N-dimethylamino-1,3-butadiene.

EXAMPLE 4

186 parts of N,N-(3-chloro-3-methoxy-propylidene)-N,N-dimethylammonium chloride, 80 parts of malodinitrile and 500 parts of methanol are refluxed for 4 hours. Working up according to Example 1(b) gives 123 parts (84% of theory) of 1,1-dicyano-4-N,N-dimethylamino-1,3-butadiene.

EXAMPLE 5 (USE)

17.3 parts of 4-dimethylamino-1,1-dicyano-1,3-butadiene and 90 parts of methanol are combined in a stirred autoclave. 16 parts of liquid ammonia are added and the mixture is stirred at 150° C. for 3 hours. The mixture is evaporated down under reduced pressure and, after the addition of ethanol, the precipitate is filtered off with suction and dried. 12.7 parts (91% of theory) of 2-aminonicotine nitrile, of melting point 130° to 132° C. (from ethanol), are obtained.

EXAMPLE 6 (USE)

19.2 parts of 4-N,N-diisobutylamino-1,1-dicyano-1,3-butadiene, 80 parts of methanol and 21 parts of ammonia are heated at 150° C. for 3 hours, according to Example 2. After the mixture has been cooled, the solvent is distilled off, 22 parts of water and 3.7 parts of sodium hydroxide are added and the mixture is refluxed for 5 hours. After cooling, the pH is adjusted to 5 with 10 percent strength HCl solution, the mixture is again cooled and the precipitate is separated off. 8.1 parts (71% of theory) of aminonicotinic acid, of melting point 305°–310° C., are obtained.

We claim:

1. A process for the preparation of a butadiene dinitrile of the formula

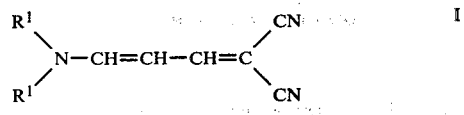

where the radicals $R^1$ are identical or different and each is an unsubstituted alkyl of 1 to 11 carbon atoms or an alkyl of 1 to 7 carbon atoms substituted by alkoxy of 1 to 4 carbon atoms, wherein a quaternary ammonium compound of the formula

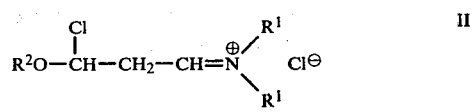

where $R^1$ has the above meaning and $R^2$ is an unsubstituted alkyl of 1 to 11 carbon atoms or an alkyl of 1 to 7 carbon atoms substituted by alkoxy of 1 to 4 carbon atoms, (a) is reacted with malodinitrile in the presence of an alkanol of 1 to 10 carbons at a temperature of about 40° to 140° C. and (b) the reaction mixture is then reacted with an alkali metal hydroxide, carbonate or alcoholate at a temperature of about −10° to +50° C.

2. A process as defined in claim 1, wherein the reaction is carried out using from 0.5 to 3 moles of malodinitrile per mole of starting material II.

3. A process as defined in claim 1, wherein the reaction is carried out using from 1 to 1,000 moles of alkanol per mole of starting material II.

4. A process as defined in claim 1, wherein the reaction is carried out using from 5 to 500 moles of water per mole of starting material II.

5. A process as defined in claim 1, wherein the reaction is carried out using from 0.2 to 10 equivalents of said alkali metal hydroxide, carbonate or alcoholate per mole of starting material II.

6. A process as defined in claim 1, wherein $R^1$ and $R^2$ are the same or different and each is an alkyl of 1 to 4 carbon atoms.

7. A process as defined in claim 1, wherein $R^1$ and $R^2$ are the same or different and each is methyl or ethyl.

8. A process as defined in claim 1, wherein the alkanol is distilled off before step (b).

* * * * *